US011490821B2

(12) United States Patent
Chen et al.

(10) Patent No.: US 11,490,821 B2
(45) Date of Patent: Nov. 8, 2022

(54) NON-CONTACT NECK-BASED RESPIRATORY AND PULSE SIGNAL DETECTION METHOD, APPARATUS, AND IMAGING DEVICE

(71) Applicant: Tsinghua University, Beijing (CN)

(72) Inventors: Huijun Chen, Beijing (CN); Chunyao Wang, Beijing (CN); Chen Zhang, Beijing (CN); Haikun Qi, Beijing (CN); Qiang Zhang, Beijing (CN); Yajie Wang, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 318 days.

(21) Appl. No.: 16/759,985

(22) PCT Filed: Oct. 24, 2018

(86) PCT No.: PCT/CN2018/111707
§ 371 (c)(1),
(2) Date: Apr. 28, 2020

(87) PCT Pub. No.: WO2019/085805
PCT Pub. Date: May 9, 2019

(65) Prior Publication Data
US 2020/0329976 A1 Oct. 22, 2020

(30) Foreign Application Priority Data
Oct. 30, 2017 (CN) .......................... 201711034416.5

(51) Int. Cl.
A61B 5/0205 (2006.01)
A61B 5/00 (2006.01)
A61B 5/055 (2006.01)

(52) U.S. Cl.
CPC .......... A61B 5/0205 (2013.01); A61B 5/0064 (2013.01); A61B 5/0073 (2013.01); A61B 5/0077 (2013.01); A61B 5/0082 (2013.01); A61B 5/055 (2013.01)

(58) Field of Classification Search
None
See application file for complete search history.

(56) References Cited

FOREIGN PATENT DOCUMENTS

| CN | 101813462 | 8/2010 |
| CN | 107550467 | 1/2018 |
| CN | 107843863 | 3/2018 |
| WO | WO2016187461 | 11/2016 |

OTHER PUBLICATIONS

English Translation of CN101813462A; 2010.*
NPL, ISR for PCT/CN2018/111707, Feb. 13, 2019.

* cited by examiner

Primary Examiner — Shahdeep Mohammed
(74) Attorney, Agent, or Firm — Hodgson Russ LLP

(57) ABSTRACT

The present disclosure provides a non-contact neck-based respiratory and pulse signal detection method and apparatus, and an imaging device. The method includes: acquiring 3D morphological information of a neck of a human body in real-time; and acquiring a respiratory signal and an electrocardiogram signal of the human body on the basis of the 3D morphological information of the neck.

8 Claims, 3 Drawing Sheets

NON-CONTACT NECK-BASED RESPIRATORY AND PULSE SIGNAL DETECTION METHOD, APPARATUS, AND IMAGING DEVICE

CROSS-REFERENCE TO RELATED APPLICATION

This application is a U.S. national phase application of International Application No. PCT/CN2018/111707, filed Oct. 24, 2018, which claims priority to Chinese Patent Application No. 201711034416.5, filed Oct. 30, 2017, the entire disclosures of which are incorporated herein by reference.

TECHNICAL FIELD

The present disclosure relates to the medical technology field, and more particularly, to a non-contact neck-based respiratory and pulse signal detection method and apparatus, and an imaging device.

BACKGROUND

Physiological signals from the body, especially respiratory and pulse signals, play an important role in many medical imaging devices. For example, in CT and magnetic resonance imaging, detecting respiratory and pulse signals can correctly control the imaging process and improve the imaging quality. Because the imaging speed of many imaging device is limited by a physical principle or technology, in many imaging devices in clinical use, using the respiration signal to perform gating imaging is the key to successfully image the lungs and liver. Regarding the cardiac imaging under the disturbance of continuous heartbeat, it will more rely on accurately obtaining the respiratory and pulse signals. The same is true for magnetic resonance imaging of the neck, where the carotid artery could beat with the pulse and the laryngeal tissue could move with the breath.

In the related art, one of the common-used respiratory signal acquisition technique mainly depends on the respiratory belt, which was placed around the thorax or abdomen to obtain the respiratory signals according to the changes of pressure or electronic property of belt with respiratory motion. However, it needs to place an additional belt before the patient positioning, and for quiet breathing, detection accuracy is not enough. In recent years, there have been a few studies of using optical methods to obtain respiratory signals based on the chest or abdomen surface movement, but they have not been integrated with imaging system, and there is no precedent for measurement based on the neck area. Pulse signal detection is mainly through electrocardiogram or detecting finger pulses, operation of which is relatively complex, participants wearing contact device for a long time will feel discomfort. More importantly, during the neck imaging, there is certain delay between the respiratory signal measured from the chest or abdomen area with the pulse signal measured by the finger-pulsometer, which will be an essential problem for imaging gating and reconstruction process.

SUMMARY

Embodiments of an aspect of the present disclosure provide a non-contact optic-based and neck-based respiratory and pulse signal detection method, including steps of: acquiring 3D morphological information of a neck of a human body; and obtaining a respiratory signal and an electrocardiogram signal of the human body according to the 3D morphological information of the neck of the human body.

Embodiments of another aspect of the present disclosure provide a non-contact optic-based and neck-based respiratory and pulse signal detection apparatus, including a processor and a memory. The memory is configured to store instructions executable by the processor. The processor is configured to run a program corresponding to the instructions by reading the instructions stored in the memory, so as to: acquire 3D morphological information of a neck of a human body; and obtain a respiratory signal and an electrocardiogram signal of the human body according to the 3D morphological information of the neck of the human body.

Embodiments of yet another aspect of the present disclosure provide a medical imaging device, including a camera, a projector and a processor. The projector is configured to project structured light towards a neck of a human body, in which light emitted by the projector is visible light or invisible infrared light, and the visible light or invisible infrared light is constant structured light. The camera is configured to photograph an optical pattern of the neck of the human body. The processor is configured to obtain 3D morphological information of the neck of the human body based on the optical pattern photographed by the camera, and to obtain a respiratory signal and an electrocardiogram signal of the human body according to the 3D morphological information of the neck of the human body.

Additional aspects and advantages of the present disclosure will be given in the following description, and some of them will become apparent from the following description or be known through the practice of the present disclosure.

BRIEF DESCRIPTION OF THE DRAWINGS

The foregoing and/or additional aspects and advantages of the present disclosure will become apparent and easy to understand from the following description of embodiments in combination with the accompanying drawings, in which.

DETAILED DESCRIPTION

Embodiments of the present disclosure are described in detail below. Examples of embodiments are shown in the attached drawings, where identical or similar reference numbers throughout indicate identical or similar elements or elements having the same or similar functions. The embodiments described below with reference to the accompanying drawings are exemplary and are intended to be used to interpret the present disclosure and cannot be construed as a limitation of the present disclosure.

The non-contact optic-based and neck-based respiratory and pulse signal detection method and apparatus and imaging device provided according to embodiments of the present disclosure will be described below with reference to the accompanying drawings. First, the non-contact optic-based and neck-based respiratory and pulse signal detection method provided according to embodiments of the present disclosure will be described with reference to drawings.

Figure 1:
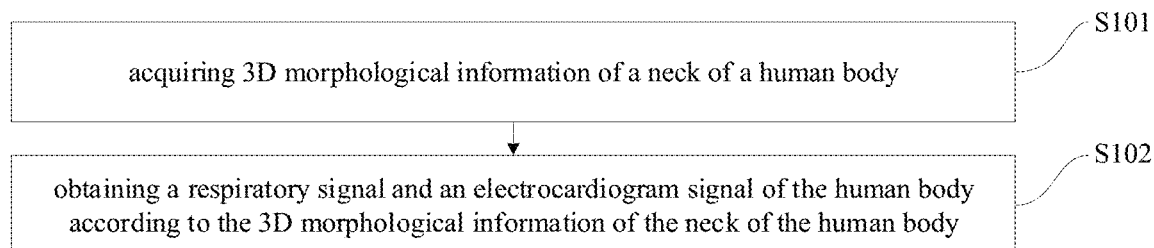
FIG. 1 is a flowchart of a non-contact optic-based and neck-based respiratory and pulse signal detection method according to an embodiment of the present disclosure.

FIG. 1 is a flowchart of a non-contact optic-based and neck-based respiratory and pulse signal detection method according to an embodiment of the present disclosure.

As illustrated in FIG. 1, the non-contact optic-based and neck-based respiratory and pulse signal detection method includes following steps.

At step S101, 3D morphological information of a neck of a human body is acquired.

In an embodiment of the present disclosure, acquiring the 3D morphological information of the neck of the human body includes: obtaining a height of the neck of the human body by making a line connecting optical centers of a camera and a projector to be parallel to a reference plane, and making an optical axis of the camera to be vertical to the reference plane.

Figure 2:
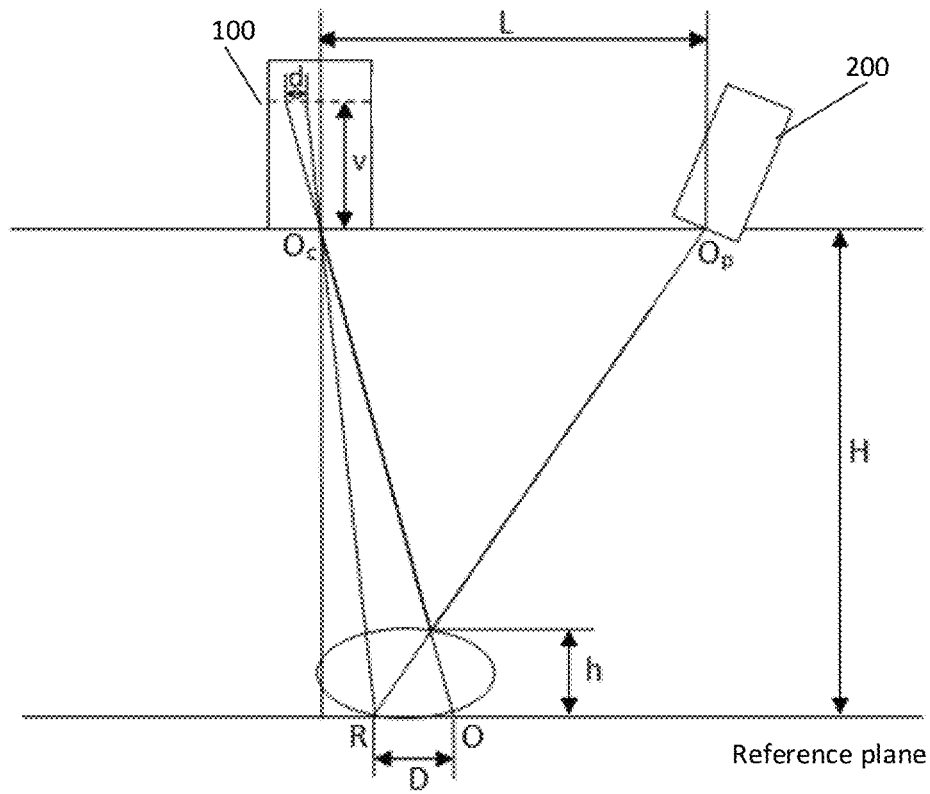
FIG. 2 is a schematic diagram of a non-contact optic-based and neck-based respiratory and pulse signal detection apparatus according to a specific embodiment of the present disclosure.

As illustrated in FIG. 2, it may be understood that, in order to obtain the height h of the neck of the human body, in embodiments of the present disclosure, the measurement may be simplified, for example, the line $O_cO_p$ connecting optical centers of the camera and the projector may be parallel to the reference plane, and the optical axis of the camera may be vertical to the reference plane.

Further, in an embodiment of the present disclosure, the height of the neck of the human body is obtained by the following formula:

$$h = \frac{H*H*d}{v*L + H*d}$$

where, H is the distance between axes of the camera and the projector, L is the distance from the camera to the reference plane, d is the aberration, and v is the image distance.

As illustrated in FIG. 2, it may be understood that, in embodiments of the present disclosure, the height h of the neck of the human body may be obtained according to the Similar Principle of Triangle:

$$\frac{H-h}{h} = \frac{L}{D} \quad (1)$$

where, D is the distance between the location R where the camera can see the light emitted by the projector without an object in the system and the location O where the camera can see the light emitted by the projector with the object placed in the system. Assuming that the camera adopts the principle of convex lens imaging and the image distance is v, then D may be obtained according to the aberration d obtained by the camera:

$$\frac{D}{d} = \frac{H}{v} \quad (2)$$

The height h of the neck of the human body may be derived from formulas (1) and (2):

$$h*L = (H-h)*D$$

$$h*L + h*D = H*D$$

$$h = \frac{H*D}{L+D}, D = H*d/v$$

$$h = \frac{H*H*d}{v*L + H*d}$$

It may be understood that, if the parameters H, v and L may be determined through calibration and known standard pattern, the actual height h of points on the object surface may be calculated by measuring the aberration d of the laser projection on the reference plane and the object surface photographed by the camera, and the length and width of the object surface may also be calculated according to corresponding parameters.

Further, in an embodiment of the present disclosure, the method may further include: projecting, by the projector, structured light covering full view towards the neck of the human body, in which light emitted by the projector is visible light or invisible infrared light, and the visible light or invisible infrared light is constant structured light; and obtaining the 3D morphological information of the neck of the human body by processing and identifying an optical pattern photographed by the camera and in combination with morphology parameters obtained after calibration.

Figure 3A:
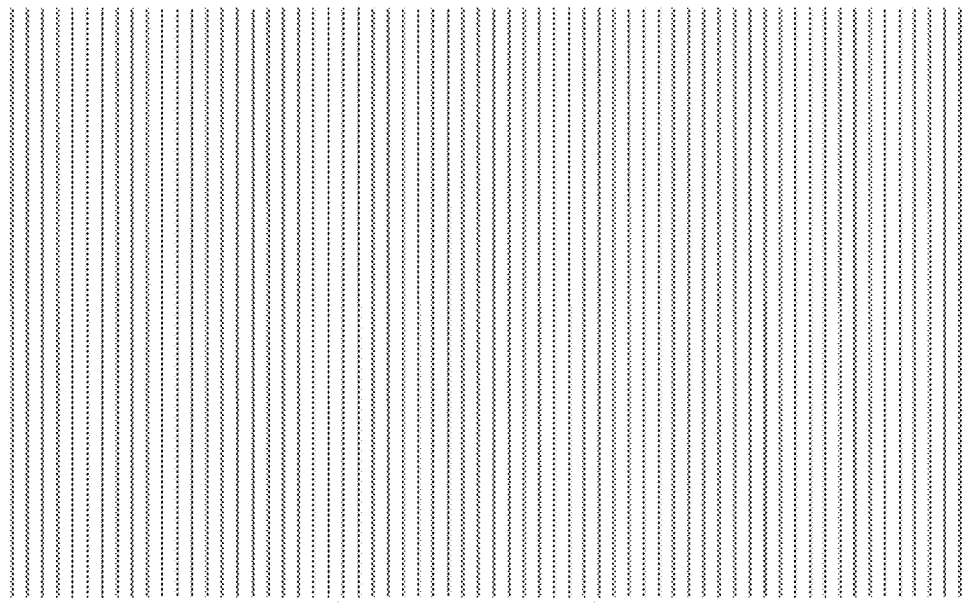
FIG. 3 is a schematic diagram illustrating a pattern of structured light according to an embodiment of the present disclosure.
Figure 3B:
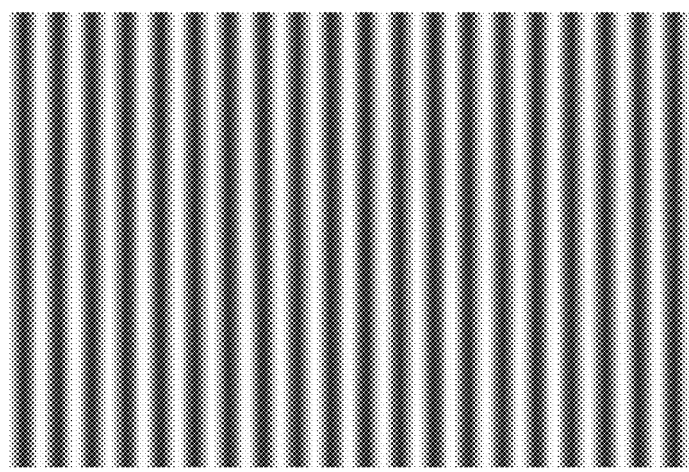

It may be understood that, in embodiments of the present disclosure, a projector (such as a laser projector) may be used to project the panoramic structured light on the neck of the human body, and as long as the area can be projected by the projector and photographed by the camera, its 3D morphology may be measured in embodiments of the present disclosure. The light emitted by the projector may be visible light or invisible infrared light, and the emission pattern of which may be constant structured light, as shown in FIG. 3, in which FIG. 3(a) shows an example of parallel structured light pattern that can work, and FIG. 3(b) shows a sine-wave structured light. In addition, the light emitted by the projector may also be of other patterns, for example, may be random code structured light. In embodiments of the present disclosure, the optical pattern photographed by the camera may be processed and identified, and in combination with the corresponding parameters calculated through the system calibration process, the 3D morphology of the whole scene may be reconstructed, which makes the operation relatively simple, and may correctly control the imaging process, and thus reduce the problems in guiding the imaging process.

In addition, in the method according to embodiments of the present disclosure, since there is no need for multiple projections, the 3D morphology measurement may be performed with high temporal resolution, which depends on the speed that the camera may acquire sharp images. In this way, it ensures that, in the method according to embodiments of the present disclosure, the 3D morphology of the human body may be measured in real time, which may correctly control the imaging process, improve the imaging quality, and reduce the problems in guiding the imaging process.

At step S102, a respiratory signal and an electrocardiogram signal of the human body is obtained according to the 3D morphological information of the neck of the human body.

Figure 4:
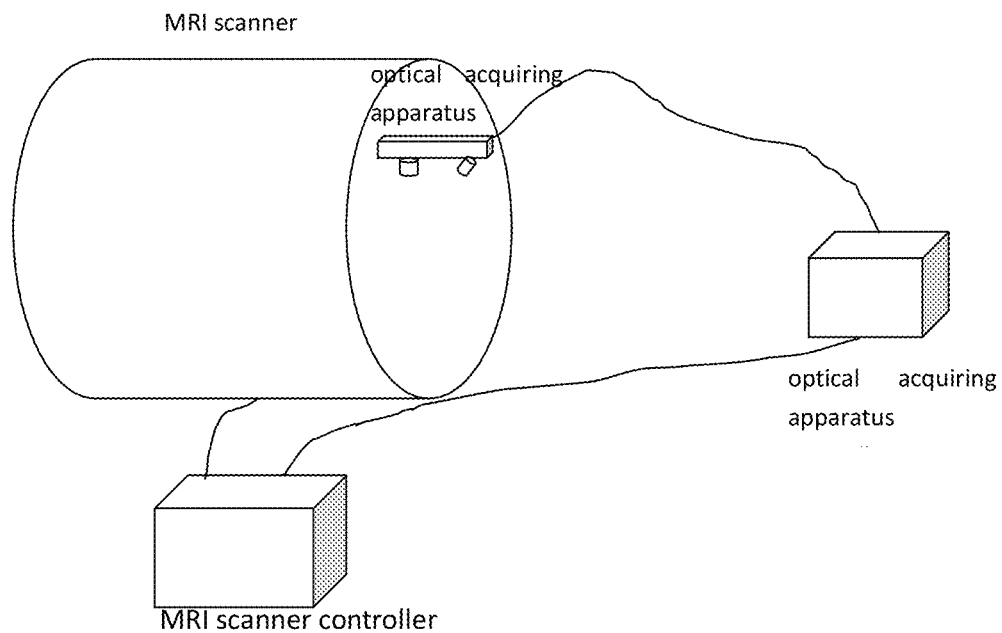
FIG. 4 is a schematic diagram of a control module according to an embodiment of the present disclosure.

It may be understood that, in order to acquire the respiratory signal and the electrocardiogram signal, in the method according to embodiments of the present disclosure, the frame rate at which the camera acquires sharp images may be between 500 frames and 1000 frames per second, thereby reducing the delay of measuring the respiratory signal and the electrocardiogram signal of the human body, and effectively improving the measurement accuracy. The location of the camera in embodiments of the present disclosure may be as shown in FIG. 4, which is not limited herein.

With the non-contact optic-based and neck-based respiratory and pulse signal detection method according to embodiments of the present disclosure, the 3D morphological information of the neck of the human body may be acquired, and the respiratory signal and the electrocardiogram signal of the human body may be obtained according to the 3D morphological information of the neck of the human body, which reduces the delay of measuring the respiratory signal and the electrocardiogram signal of the human body, and effectively improves the measurement accuracy, and moreover, not only is easy to operate, and realizes non-contact measurement, but also may measure the 3D morphology of the neck of the human body in real time, thereby controlling the imaging process correctly, improving the imaging quality, and reducing the problems in guiding the imaging process.

Next, the non-contact optic-based and neck-based respiratory and pulse signal detection apparatus provided according to embodiments of the present disclosure will be described with reference to drawings.

Figure 5:
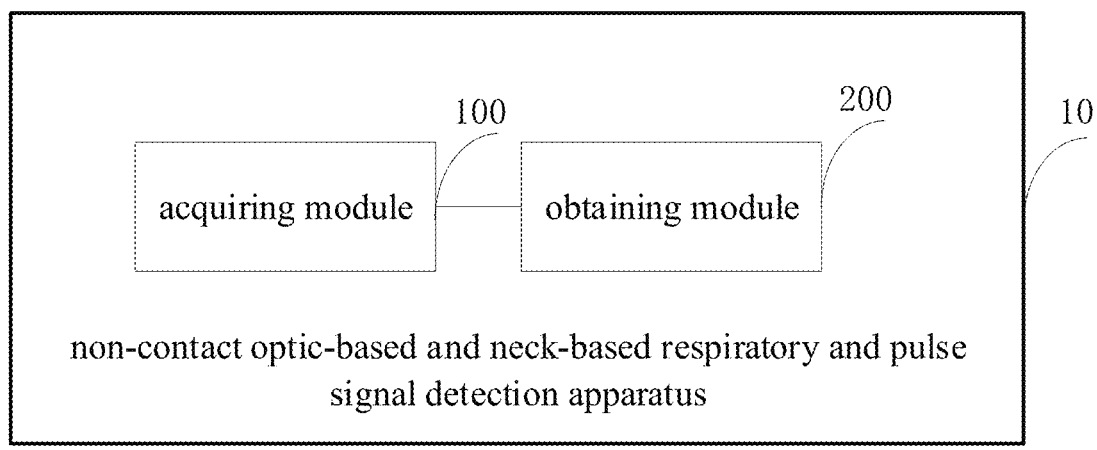
FIG. 5 is a block diagram of a non-contact optic-based and neck-based respiratory and pulse signal detection apparatus according to embodiments of the present disclosure.

FIG. 5 is a block diagram of a non-contact optic-based and neck-based respiratory and pulse signal detection apparatus according to embodiments of the present disclosure.

As illustrated in FIG. 5, the non-contact optic-based and neck-based respiratory and pulse signal detection apparatus 10 includes an acquiring module 100 and an obtaining module 200.

The acquiring module 100 is configured to acquire 3D morphological information of a neck of a human body. The obtaining module 200 is configured to obtain a respiratory signal and an electrocardiogram signal of the human body according to the 3D morphological information of the neck of the human body. The apparatus 10 according to embodiments of the present disclosure may obtain the respiratory signal and the electrocardiogram signal of the human body according to the 3D morphological information of the neck of the human body, which not only reduces the delay of measuring the respiratory signal and the electrocardiogram signal of the human body, thereby improving the measurement accuracy, but also may control the imaging process correctly, improving the imaging quality.

In an embodiment of the present disclosure, the acquiring module 100 includes a camera, a projector, and an acquiring unit. The acquiring unit is configured to obtain a height of the neck of the human body by making a line connecting optical centers of a camera and a projector to be parallel to a reference plane, and making an optical axis of the camera to be vertical to the reference plane.

Further, in an embodiment of the present disclosure, the acquiring unit may obtain the height of the neck of the human body by the following formula:

$$h = \frac{H*H*d}{v*L+H*d}$$

where, H is the distance between axes of the camera and the projector, L is the distance from the camera to the reference plane, d is the aberration, and v is the image distance.

As illustrated in FIG. 2, it may be understood that, in embodiments of the present disclosure, the height h of the neck of the human body may be obtained according to the Similar Principle of Triangle:

$$\frac{H-h}{h} = \frac{L}{D} \quad (1)$$

where, D is the distance between the location R where the camera can see the light emitted by the projector without an object in the system and the location O where the camera can see the light emitted by the projector with the object placed in the system. Assuming that the camera adopts the principle of convex lens imaging and the image distance is v, then D may be obtained according to the aberration d obtained by the camera:

$$\frac{D}{d} = \frac{H}{v} \quad (2)$$

The height h of the neck of the human body may be derived from formulas (1) and (2):

$$h*L = (H-h)*D$$

$$h*L + h*D = H*D$$

$$h = \frac{H*D}{L+D}, D = H*d/v$$

$$h = \frac{H*H*d}{v*L+H*d}$$

It may be understood that, if the parameters H, v and L may be determined through calibration and known standard pattern, the actual height h of points on the object surface may be calculated by measuring the aberration d of the laser projection on the reference plane and the object surface photographed by the camera, and the length and width of the object surface may also be calculated according to corresponding parameters.

Further, in an embodiment of the present disclosure, the apparatus 10 may further include a control unit and an obtaining unit.

The control unit is configured to control the projector to project structured light covering full view towards the neck of the human body, in which light emitted by the projector is visible light or invisible infrared light, and the visible light or invisible infrared light is constant structured light. The obtaining unit is configured to obtain the 3D morphological information of the neck of the human body by processing and identifying an optical pattern photographed by the camera and in combination with morphology parameters obtained after calibration.

It may be understood that, in embodiments of the present disclosure, the control unit may control the projector (such as a laser projector) to project the panoramic structured light on the neck of the human body, and as long as the area can be projected by the projector and photographed by the camera, its 3D morphology may be measured in embodiments of the present disclosure. The light emitted by the projector may be visible light or invisible infrared light, and the emission pattern of which may be constant structured light, as shown in FIG. 3, in which FIG. 3(a) shows an example of parallel structured light pattern that can work, and FIG. 3(b) shows a sine-wave structured light. In addition, the light emitted by the projector may also be of other patterns, for example, may be random code structured light. The obtaining unit may process and identify the optical pattern photographed by the camera, and in combination with the corresponding parameters calculated through the system calibration process, reconstructs the 3D morphology of the whole scene, which makes the operation relatively simple, and may correctly control the imaging process, and thus reduce the problems in guiding the imaging process.

With the non-contact optic-based and neck-based respiratory and pulse signal detection apparatus according to embodiments of the present disclosure, the 3D morphological information of the neck of the human body may be acquired, and the respiratory signal and the electrocardiogram signal of the human body may be obtained according to the 3D morphological information of the neck of the human body, which reduces the delay of measuring the respiratory signal and the electrocardiogram signal of the human body, and effectively improves the measurement accuracy, and moreover, not only is easy to operate, and realizes non-contact measurement, but also may measure the 3D morphology of the neck of the human body in real time, thereby controlling the imaging process correctly, improving the imaging quality, and reducing the problems in guiding the imaging process.

Furthermore, embodiments of the present disclosure provide a medical imaging device. The medical imaging device includes the non-contact optic-based and neck-based respiratory and pulse signal detection apparatus described above. The medical imaging device may acquire the 3D morphological information of the neck of the human body, and may obtain the respiratory signal and the electrocardiogram signal of the human body according to the 3D morphological information of the neck of the human body, which reduces the delay of measuring the respiratory signal and the electrocardiogram signal of the human body, and effectively improves the measurement accuracy, and moreover, not only is easy to operate, and realizes non-contact measurement, but also may measure the 3D morphology of the neck of the human body in real time, thereby controlling the imaging process correctly, improving the imaging quality, and reducing the problems in guiding the imaging process.

In the description of the present disclosure, it is to be understood that a location or position relation indicated by the term "center", "longitudinal", "lateral", "length", "width", "thickness", "up", "down", "front", "rear", "left", "right", "vertical", "horizontal", "top", "bottom" "inside", "outside", "clockwise", "anticlockwise", "axial", "radial" and "circumferential" is the location or position relation shown in the appended drawings, and is only to facilitate the description of the present disclosure and simplify the description, rather than indicating or implying that the device or element referred to must have a particular orientation, be constructed and operated in a particular orientation, and therefore cannot be construed as a limitation of the present disclosure.

In addition, the terms "first" and "second" are used for description purposes only and cannot be understood to indicate or imply relative importance or to imply the number of technical features indicated. Thus, a feature that is defined as "first" or "second" may explicitly or implicitly include at least one of these features. In the description of the present disclosure, "multiple" means at least two, e.g., two, three, etc., unless otherwise specified specifically.

In the present disclosure, the terms "installed", "connected", "coupled" and "fixed" shall be understood in a broad sense, for example, it may be a fixed connection, it may be a detachable connection, or it may be an integral part; it may be mechanical or electrical; it may be either direct connection or indirectly connection via an intermediary, or it may be a connection between two elements or an interaction between two elements, unless otherwise defined. For ordinary technicians in the field, the specific meaning of the above terms in the present disclosure can be understood according to specific circumstances.

In the present disclosure, unless otherwise specified and limited, the first feature "above" or "below" the second feature may be a direct contact between the first and second features, or an indirect contact between the first and second features through an intermediate medium. Moreover, the first feature is "above", "over" and "on" the second feature may refer to that the first feature is directly above or obliquely above the second feature, or simply means that the first feature is higher than the second feature. The first feature "below", "under", and "at the bottom of" the second feature may be that the first feature is directly below or diagonally below the second feature, or simply means that the horizontal height of the first feature is less than that of the second feature.

Reference throughout this specification to "an embodiment," "some embodiments," "an example," "a specific example," or "some examples," means that a particular feature, structure, material, or characteristic described in connection with the embodiment or example is included in at least one embodiment or example of the present disclosure. The appearances of the above phrases in various places throughout this specification are not necessarily referring to the same embodiment or example of the present disclosure. Furthermore, the particular features, structures, materials, or characteristics may be combined in any suitable manner in one or more embodiments or examples. In addition, different embodiments or examples and features of different embodiments or examples described in the specification may be combined by those skilled in the art without mutual contradiction.

Although embodiments of present disclosure have been shown and described above, it should be understood that above embodiments are just explanatory, and cannot be construed to limit the present disclosure, for those skilled in the art, changes, alternatives, and modifications can be made to the embodiments without departing from spirit, principles and scope of the present disclosure.

What is claimed is:

1. A non-contact optic-based and neck-based respiratory and pulse signal detection method, comprising:
   acquiring three-dimensional (3D) morphological information of a neck of a human body; and
   obtaining a respiratory signal and an electrocardiogram signal of the human body according to the 3D morphological information of the neck of the human body;
   wherein acquiring the 3D morphological information of the neck of the human body, comprises: obtaining a height h of the neck of the human body by making a line connecting optical centers of a camera and a projector to be parallel to a reference plane, and making an optical axis of the camera to be vertical to the reference plane;
   wherein the height h of the neck of the human body is calculated by $$h = \frac{H*H*d}{v*L+H*d},$$

where H is a distance between axes of the camera and the projector, L is a distance from the camera to the reference plane, v is an image distance, and d is an aberration of laser projection on the reference plane and an object surface photographed by the camera.

2. The method of claim 1, further comprising:
projecting, by the projector, structured light covering full view towards the neck of the human body, in which light emitted by the projector is visible light or invisible infrared light, and the visible light or invisible infrared light is constant structured light; and
obtaining the 3D morphological information of the neck of the human body by processing and identifying an optical pattern photographed by the camera and in combination with morphology parameters obtained by calibration.

3. The method of claim 1, wherein H, v, and L are determined through calibration and a known standard pattern.

4. A non-contact optic-based and neck-based respiratory and pulse signal detection apparatus, comprising:
a processor; and
a memory, configured to store instructions executable by the processor,
wherein the processor is configured to run a program corresponding to the instructions by reading the instructions stored in the memory, so as to:
acquire three-dimensional (3D) morphological information of a neck of a human body; and
obtain a respiratory signal and an electrocardiogram signal of the human body according to the 3D morphological information of the neck of the human body;
wherein the processor is configured to acquire the 3D morphological information of the neck of the human body by obtaining a height h of the neck of the human body by controlling a line connecting optical centers of a camera and a projector to be parallel to a reference plane, and controlling an optical axis of the camera to be vertical to the reference plane;
wherein the height h of the neck of the human body is calculated by $$h = \frac{H*H*d}{v*L+H*d},$$

where H is a distance between axes of the camera and the projector, L is a distance from the camera to the reference plane, v is an image distance, and d is an aberration of laser projection on the reference plane and an object surface photographed by the camera.

5. The apparatus of claim 4, wherein the processor is further configured to:
control the projector to project structured light covering full view towards the neck of the human body, in which light emitted by the projector is visible light or invisible infrared light, and the visible light or invisible infrared light is constant structured light; and
obtain the 3D morphological information of the neck of the human body by processing and identifying an optical pattern photographed by the camera and in combination with morphology parameters obtained when calibration.

6. The apparatus of claim 4, wherein H, v, and L are determined through calibration and a known standard pattern.

7. A medical imaging device, comprising:
a projector, configured to project structured light towards a neck of a human body, in which light emitted by the projector is visible light or invisible infrared light, and the visible light or invisible infrared light is constant structured light;
a camera, configured to photograph an optical pattern of the neck of the human body;
a controller, configured to control a line connecting optical centers of the camera and the projector to be parallel to a reference plane, and control an optical axis of the camera to be vertical to the reference plane; and
a processor, configured to obtain three-dimensional (3D) morphological information of the neck of the human body based on the optical pattern photographed by the camera, and to obtain a respiratory signal and an electrocardiogram signal of the human body according to the 3D morphological information of the neck of the human body;
wherein the processor is configured to obtain the 3D morphological information of the neck of the human body by obtaining a height h of the neck of the human body by $$h = \frac{H*H*d}{v*L+H*d},$$

where H is a distance between axes of the camera and the projector, L is a distance from the camera to the reference plane, v is an image distance, and d is an aberration of laser projection on the reference plane and an object surface photographed by the camera.

8. The medical imaging device of claim 7, wherein H, v, and L are determined through calibration and a known standard pattern.

* * * * *